United States Patent
Amaldi

(10) Patent No.: US 7,554,275 B2
(45) Date of Patent: Jun. 30, 2009

(54) PROTON ACCELERATOR COMPLEX FOR RADIO-ISOTOPES AND THERAPY

(75) Inventor: Ugo Amaldi, Geneva (CH)

(73) Assignee: Fondazione per Adroterapia Oncologica - TERA, Novara (NO) (IT)

( * ) Notice: Subject to any disclaimer, the term of this patent is extended or adjusted under 35 U.S.C. 154(b) by 384 days.

(21) Appl. No.: 11/439,132

(22) Filed: May 24, 2006

(65) Prior Publication Data

US 2007/0108922 A1    May 17, 2007

(30) Foreign Application Priority Data

Nov. 11, 2005  (IT) .............................. CO05A0028

(51) Int. Cl.
H05H 9/00  (2006.01)

(52) U.S. Cl. ........................ 315/505; 315/507; 315/500; 250/492.3

(58) Field of Classification Search ................ 315/5.42, 315/500, 502, 503, 505–507; 250/423, 492.1, 250/492.3

See application file for complete search history.

(56) References Cited

U.S. PATENT DOCUMENTS

| 5,260,581 A * | 11/1993 | Lesyna et al. | 250/492.3 |
| 6,809,325 B2 * | 10/2004 | Dahl et al. | 250/492.3 |
| 2004/0108823 A1 | 6/2004 | Amaldi et al. | |

FOREIGN PATENT DOCUMENTS

| FR | 2 737 834 | 2/1997 |
| WO | WO 2004/101070 | 11/2004 |
| WO | WO 2006/081847 | 8/2006 |

OTHER PUBLICATIONS

Amaldi U. "Nuclear physics applications in diagnostics and cancer therapy" Nuclear Physics A Elsevier Netherlands, vol. 751, Apr. 18, 2005, pp. 409-428.

Amaldi U. et al. "LIBO-a linac-booster for protontherapy: construction and tests of a prototype" Nuclear Instruments & Methods in Physics Research, Section—A: Accelerators, Spectrometers, Detectors and Associated Equipment, Elsevier, Amsterdam, NL, vol. 521, No. 2-3 Apr. 1, 2004 512-529.

Bol J.L. et al. "High intensity H<->cyclotrons for radioisotope production" Proceedings of the 1989 IEEE Particle Accelerator Conference. Accelerator Science and Technology IEEE New York 1989 pp. 764-766.

De Martinis C. et al. "Beam tests on a proton linac booster for hadron therapy" 8th European Particle Accelerator Conference Eur. Phys. Soc Geneva, Switzerland 2002 pp. 2727-2729.

Yokota W. et al. "Performance and operation of a beam chopping system for a cyclotron with multiturn extraction" Review of Scientific Instruments AIP USA vol. 68 No. 4 Apr. 1997 pp. 1714-1719.

Zennaro R. "IDRA: design study of a protontherapy facility" ICFA Beam Dynamics Newsletter No. 36 Apr. 1, 2005 pp. 62-72.

* cited by examiner

Primary Examiner—Haissa Philogene
(74) Attorney, Agent, or Firm—Young & Thompson

(57) ABSTRACT

A complex of proton accelerators, includes the following functionally interconnected components: a proton source, a cyclotron, at least one target, located either internally or externally to the cyclotron, a medium energy beam transport magnetic channel, a radiofrequency linear accelerator, a high energy beam transport channel towards an area dedicated to the irradiation of tumors with proton beams, as well as a modular system for supplying radio frequency power capable of feeding, independently two or more accelerating modules of the linac. An integrated computerized system controls the complex of accelerators so to carry out, either in alternation or simultaneously, both the production of radioisotopes—for medical, industrial and therapeutical purposes—and the therapeutical irradiation of, even deep seated tumors. The complex of accelerators produces proton beams which, applying the recently developed 'spot scanning' technique, are more suited for the tumor irradiation than the ones produced by cyclotrons and synchrotrons.

21 Claims, 1 Drawing Sheet

PROTON ACCELERATOR COMPLEX FOR RADIO-ISOTOPES AND THERAPY

FIELD OF THE INVENTION

This invention refers to a complex of accelerators of proton beams, to a method and the use thereof. Referring to its functionality the proposed complex of accelerators is called PACRIT (Proton Accelerator Complex for Radio-Isotopes and Therapy).

BACKGROUND OF THE INVENTION

It is well known that the use of radiopharmaceuticals injected in the body of the patient is an essential tool in medical diagnostic and in particular in the diagnostic of tumours. Gamma scintigraphy, also named Single Photon Emission Tomography (SPET or SPECT), is the most common technique. But, in the past fifteen years, Positron Emission Tomography (PET) has spread quickly also in association with the quantitative observation of the morphology of internal organs allowed by Computerized Tomography (CT). The future of tumor diagnostic is in the use of combined devices as CT/PET and also MRI/PET (MRI=Magnetic Resonance Imaging).

These widespread diagnostic methods employ radioisotopes distributed by specialized companies and produced in nuclear reactors (Tc-99m is used for SPET) and by high current cyclotrons (F-18 is the most used isotope in PET diagnostics). Many hospitals run cyclotrons to produce locally the needed isotopes. These and other isotopes used for SPET and PET are listed in Table 1 and 2. The proton energy range is also indicated in MeV (million electron-volt).

TABLE 1

Radio-isotopes used in SPET

| Isotope | Half life | Decay | Proton energy range [MeV] | Utilization |
|---|---|---|---|---|
| $^{51}$Cr | 27.7 days | $\gamma$ | 2-30 | Tomo-scintigraphy |
| $^{67}$Ga | 3.3 days | $\gamma$ | 14-33 | Tomo-scintigraphy of lymphomas |
| $^{111}$In | 2.8 days | $\gamma$ | 13-31 | Tomo-scintigraphy of endocrine tumours |
| $^{123}$I | 13.2 hours | $\gamma$ | 13-30 | Tomo-scintigraphy |
| $^{201}$Tl | 72.9 hours | $\gamma$ | 20-40 | Tomo-scintigraphy |

TABLE 2

Radio-isotopes used in PET

| Isotope | Half life | Decay | Proton energy range [MeV] | Utilization |
|---|---|---|---|---|
| $^{11}$C | 20.4 min | $\beta$+ | 6-25 | Indicator of cellular activity |
| $^{15}$O | 2.1 min | $\beta$+ | 5-21 | Indicator of tumour necrosis |
| $^{18}$F | 109 min | $\beta$+ | 3-20 | Metabolism of the glucose |
| $^{81}$Rb | 4.6 hours | $\beta$+ | >20 | Myocardium and brain |

Others radiopharmaceuticals introduced in the body of patients (brachitherapy) are used for pain palliation and the control of primary tumours and methastases. Some of the most common and/or promising ones, which can be produced with proton beams, are listed in Table 3.

TABLE 3

Radio-isotopes produced for palliation and tumour cure.

| Isotope | Half life | Decay | Proton energy range [Mev] | Utilization |
|---|---|---|---|---|
| $^{67}$Cu | 61.9 hours | $\beta^-$ | 8-33 | Radio-immuno therapy |
| $^{153}$Sm | 46.5 hours | $\beta^-$ | >15 | Cure and pain relieve of bony metastases |
| $^{165}$Er | 10.4 hours | $e^-$ | 6-25 | Radio-immuno therapy |
| $^{166}$Ho | 26.8 hours | $\beta^-, \gamma$ | (*) | Treatment metastases and skin melanoma |
| $^{186}$Re | 90.6 hours | $\beta^-, \gamma$ | (*) | Cure and pain relieve of bony metastases |
| $^{212}$Bi | 60.6 min | $\alpha$ | (**) | Radio immuno therapy |
| $^{213}$Bi | 45.6 min | $\alpha$ | (**) | Radio immuno therapy |

(*) These isotopes can be produced with the 'Adiabatic Resonance Crossing' technique described in WO98/59347.
(**) In hospitals these isotopes are usually produced with generators bought from specialized companies but they could also be produced with 30 MeV cyclotrons.

Brachitherapy is today less common than the above said diagnostic techniques, but rapid developments are foreseen due to the availability of many isotopes, with different production mechanisms and various half-lives.

The production of many of the radioisotopes, listed as examples in Tables 1-3, requires intense proton beams of energies larger than the 10-15 MeV used for the production of the standard PET isotopes, F-18. Moreover, the production cross sections of nearly all the isotopes increase with energy so that, for a fixed proton current, the production rate increases with the energy and the use of higher energies is convenient if the simultaneous increase of the production of undesired radioisotopes can be avoided. In all cases the currents needed for these applications are at least fifty microampere.

For this reason the said high-current proton beams are valid tools in diagnostic and tumour brachytherapy. On the other hand, collimated proton beams of higher energy (up to 250 MeV) but much lower currents (nanoamperes) are used in 'protontherapy', the precision radiation therapy used also for deep seated tumours. This is the most common type of 'hadrontherapy' because it spares the healthy tissues surrounding the tumour much better than the 'X-rays' produced by 5-20 MeV electron linacs while having practically the same radiobiological and clinical effects. It is not necessary to perform many clinical trials to reach the conclusion that—since the proton dose distribution is, in all cases, more localized on the tumour target—this modality is always more favourable than the conventional ones for solid tumours located close to the organs at risk that do not have to be irradiated. The only limitations are due to the needed investments and the dimensions of the equipments which imply a treatment cost higher by a factor 2-3.

Today, on a population of 10 million inhabitants, approximately 20,000 patients are irradiated every year with X-rays. Recent studies performed in many countries have reached the conclusion that between 12% to 15% of these patients treated with protons rather than with X-rays would have such a therapeutic advantage to justify the higher cost.

From the previous considerations it is clear that proton beams produced for modern diagnostic and for therapeutic medicine need to fulfill different requirements and therefore require different proton accelerators:
1. for producing radioisotopes the energy range is 10-70 MeV and the current range is 50-1000 μA,
2. for protontherapy the energy range is 60-250 MeV and the current range is 0.1-10 nA.

Mostly cyclotrons—but occasionally also linacs—are used to accelerate protons and other types of ions for the production of radioisotopes. For protontherapy, both cyclotrons (room-temperature or super-conductive) and synchrotrons are used. Even belonging to the same hospital or centre, these accelerators are usually installed in separate buildings and are managed separately, typically the first by nuclear physicians, chemists and nuclear physicists and the second ones by radiation oncologists and medical physicists.

SUMMARY OF THE INVENTION

The basic object of the present invention is to provide a complex of proton accelerators for deep tumour tele-therapy which, being a compact facility of limited power consumption, allows also the production of radio-isotopes for diagnostics and/or therapeutical purposes. Another object is to be seen in the fact that the accelerator complex can also be used for industrial and/or physics applications as well as for the production of neutron fields used in radio-isotope production and/or Boron Neutron Capture Therapy (BNCT) and/or Boron Neutron Capture Synevectomy (BNCS).

According to the present invention, these objects are solved by a proton accelerator complex PACRIT.

According to the invention, the radio-isotopes for uses in diagnostics and/or brachitherapy and/or industry are produced by sending the protons accelerated by a cyclotron on targets internal or external to the said cyclotron. Moreover a linac accelerates one of the external beams which, after reaching the appropriate energy level, is sent to one or more patient irradiation rooms.

Said complex of accelerators and beam transport channels are under the supervision of a distributed system of computers and of appropriate software which guides—either in alternation or simoultaneously—said proton beams to the targets for the production of medical and industrial radioisotopes and to the patient irradiation rooms. The first accelerator is a high-current proton cyclotron apt to radioisotope production and the second one is a high-frequency linac which accelerates a very small fraction of one of the external cyclotron beams to the energies needed for proton therapy.

The proposed PACRIT complex produces enough radio-isotopes to serve the hospital/institute in which it is installed allowing the distribution to other centres becoming the focus of a variety of research programmes in biology, medicine, physics and engineering.

The PACRIT complex of the invention achieves many important advantages. The first one is very general: PACRIT realizes a physical and culturally interdisciplinary space which favours the development of novel diagnostics and therapy modalities since medical doctors, radiation oncologists, radiologists, nuclear physicians, medical physicists, chemists, nuclear physicists and engineers can tackle side by side the problems related to the detection and the control of tumours and their metastases. A second general advantage is due to the fact that, since PACRIT has a dual use (radio-isotope production and proton therapy) the acquisition of a higher energy cyclotron (30 MeV or 70 MeV instead than 10-15 MeV) is economically justified allowing the production of a larger variety of isotopes. These cyclotrons can also accelerate other particles (e.g. helium ions) to energies large enough to produce medical radioisotopes (as Astatine-211) which cannot be obtained with lower energy proton cyclotrons.

An important technical advantage with respect to the synchrotrons used in proton therapy is the fact that the linac has a modular structure made of many accelerating modules and thus a much smaller number of non-identical components. Moreover PACRIT does not require the complicated magnets and the electrostatic deflectors used to inject and extract the protons from a synchrotron. These components act at the beginning and at the end of an acceleration cycle so that the proton beam irradiating a patient has a cyclical structure with a dead time which is about one second long every 2-3 seconds. This time structure of the beam complicates the 'respiratory gating' often needed to irradiate only when the patient's lungs are emptied so to avoid a too large displacement of the tumour target. The therapeutic beam of the invention is instead always present and is formed by short bursts (few microseconds long) separated by a few milliseconds. This allows a respiratory gating as in a cyclotron and in the Fixed Field Alternated Gradient (FFAG) accelerators, considered for future uses in hadron therapy. This advantage is indicated in the second column of Table 4.

TABLE 4

Comparison of four types of accelerators used or proposed for proton therapy

| Accelerator | The beam is always present during treatment? | The output energy can be varied with the accelerator? | Time needed for the variation of the accelerator energy |
|---|---|---|---|
| Synchrotron | No (cycle) | Yes | 1 second |
| Cyclotron | Yes | No | — |
| FFAG | Yes | No | — |
| PACRIT | Yes | Yes | 1 millisecond |

The unique time structure of PACRIT protontherapy beams implies other advantages.

After the delivery of a proton pulse to a 'spot' of the tumour target, during the few milliseconds without protons the energy and number of the protons delivered to the next 'spot' can be adjusted according to the prescriptions of the Treatment Planning System (TPS). According to the invention the energy is varied continuously between the minimum (i.e. the cyclotron energy) and the linac maximum output energy by not sending the RF driving signal to some klystrons and/or by shifting the phase and amplitude of one of these signals. At the same time the number of protons delivered in the next spot is chosen with 3% accuracy in a range 300:1 by defocusing the electrostatic lenses of the Low Energy Beam Transfer (LEBT) system between the source and the cyclotron.

This is an important feature in the depth scanning of a tumour target since, as indicated in Table 4, cyclotrons and FFAGs produce beams of fixed energy and require the movement of absorbers to vary the penetration range in the body of the patient with a well established technique. On the other side PACRIT energy and intensity are adjusted in one millisecond and electronic controls are more reliable and require less maintenance than mechanical ones, a clear plus considering the many decades during which such a center has to run. Moreover the use of absorbers entails the production of secondary particles, mainly neutrons, which have to be shielded and can, if the energy reduction is large, induce dangerous radioactivity. From this point of view PACRIT is similar to a synchrotron, since the output energy and intensity of the machine can be varied without moving parts, with the added advantage that the adjustments require one millisecond instead of about one second. Furthermore it is worth remarking that in a cyclotron the range variation of the 200-250 MeV protons produced requires not only absorbers but also an 'Energy Selection System' (ESS) which is as long as the linac of PACRIT, so that the area needed for the buildings is not larger in spite of the dual use of the cyclotron.

A further advantage of the time structure of the beam is apparent when considering the spot scanning technique developed at the Paul Scherrer Institute in Villigen (Switzerland), where the spot is moved transversally to the beam in about two milliseconds: the time separating two successive PACRIT spots is more than enough for this active technique of depositing the dose. At PSI a time 'hole' of 5 ms is created in the cyclotron continuous beam while moving with a scanning magnet the 'spot' where the dose is deposited from one location to the next one. Instead PACRIT does not need any special intervention to have a 'hole' between two successive proton pulses. Moeover, in the spot scanning delivery the high repetition rate of the linac (hundreds of Hz) allows a large number of 'paintings' of the tumour target, a very important asset in the case of moving organs when a single painting can produce local dose depositions which are too high or too low with respect to the predictions of the Treatment Planning System.

Since many years at GSI the dose delivered by the carbon ion beam is controlled by measuring with a PET scanner located 'on beam' the distribution of the positron emitting radioisotopes produced in the irradiated tissues. Recent studies have shown that this technique can be applied to the localization of the dose deposition in the case of proton irradiations. The activity is large enough and the distal fall-off is so sharp to allow a determination of the proton range with about one millimetre accuracy. This will become a very important Quality Assurance test. PACRIT is particularly suited to such on beam PET measurement because the beam is off for more than 99% of the time. This avoids the problems caused by the accidental coincidences due to high energy photons produced in the irradiated patient during the extraction of a synchrotron beam.

All said advantages with respect to the protontherapy centres presently available commercially can be summarized by stating that PACRIT realizes a physical and cultural space where nuclear physicians, radiologists, radiation oncologists, nuclear chemists, nuclear physicians, medical physicists and medical engineers work together in the three related (but too often separated) fields of radioisotope diagnostics, brachitherapy and conformal protontherapy;

features a cyclotron having proton energies and intensities large enough to produce intense neutron radiation fields that allow new ways of producing medical radioisotopes (also for industrial uses) and of treating some tumours and other diseases (for instance with BNCT and BCNS);

produces a proton therapy beam that as far as the time and intensity structure is concerned is better suited to the spot scanning technique than both cyclotrons and synchrotrons;

is particularly suited to treat moving organs, in particular because can 'paint' many times the tumour target in synchronism, if needed, with the movements due to the respiration;

is 'active' for less than 0.1% of the time, so that there is no disturbance to data collection if a PET on-beam system is installed to verify the quality of the treatment;

can be built in successive phases, since linac modules can be added when desired, so as to spread the investment over a longer time scale while having the possibility to start radioisotope production within two years from the start of the project;

BRIEF DESCRIPTION OF THE DRAWINGS

Other advantages, details and characteristics of the accelerator complex according to the present invention will furthermore result from the following description of a preferred embodiment of the invention, schematically shown in the appended drawings in which.

DETAILED DESCRIPTION OF PREFERRED EMBODIMENTS

Figure 1:
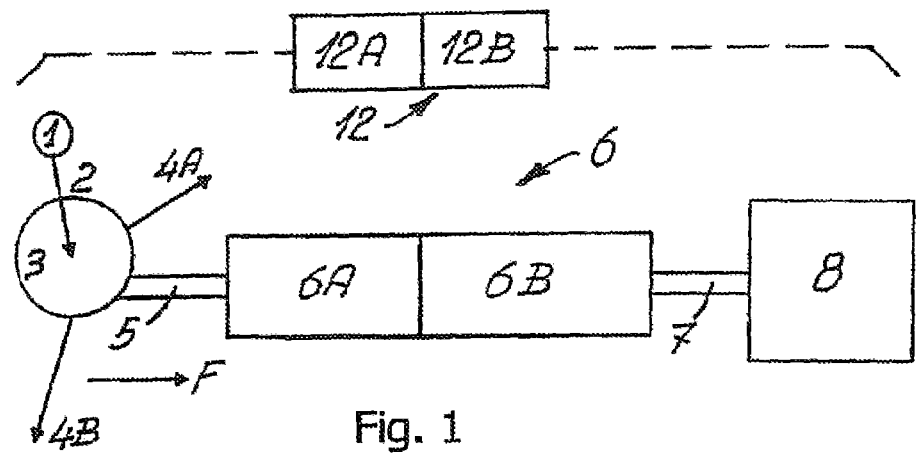
FIG. 1 is a block diagram of an accelerator complex according to the invention.
Figure 2:
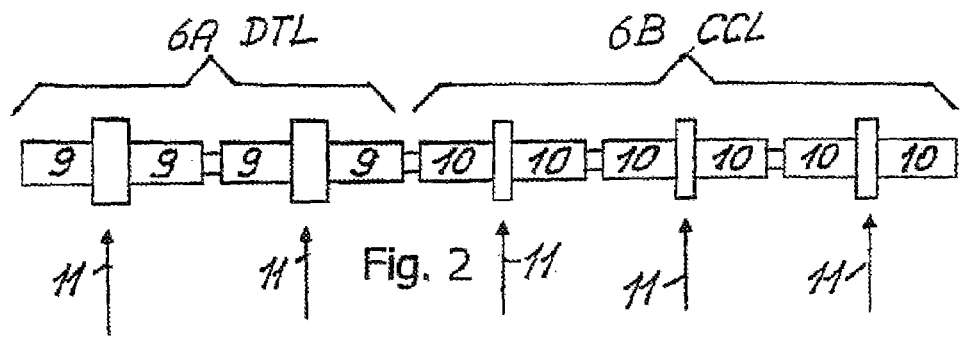
FIG. 2 is a block diagram of an embodiment of a modular linac with two sections having 2 and 3 modules, respectively.
Figure 3:
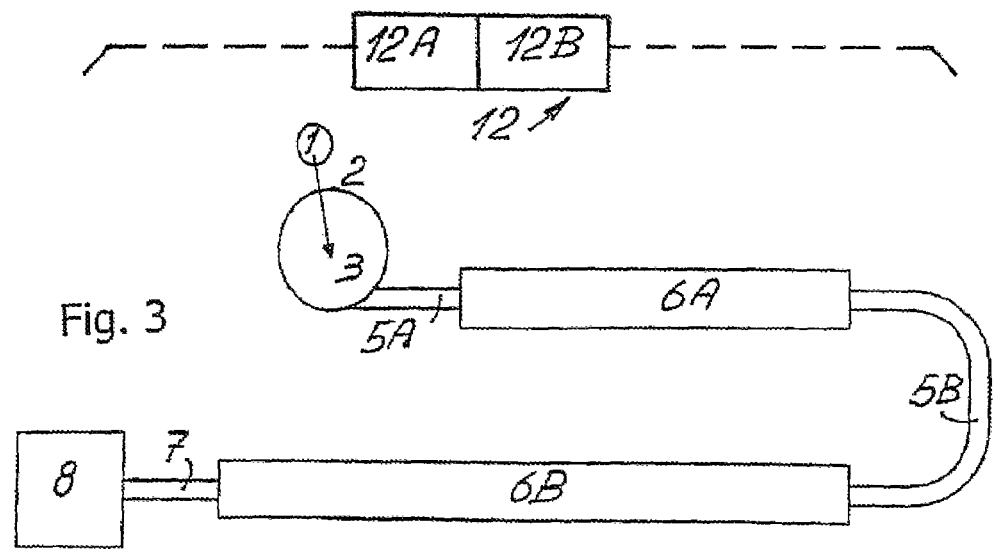
FIG. 3 is a block diagram of a variant of the proton accelerator complex according to the present invention.

The components of the proton accelerator complex for radioisotope production and proton therapy, shown in FIGS. 1-3, are the folowing:

1. proton source;
2. Low Energy Beam Transport channel (LEBT)
3. cyclotron;
4A and AB two of the many possible beam lines for the production of radioisotopes on internal and/or external targets;
5. Medium Energy Beam Transport channel (MEBT)
5A low-medium energy channel
5B medium-high energy channel;
6. high-frequency linac, with frequency typically larger than 1 GHz;
6A modular accelerating section of the Drift Tube Linac structure (DTL) of linac 6 with a number of modules depending on the application;
6B modular accelerating section of the Cavity Coupled Linac structure (CCL) of linac 6 with a number of modules depending on the application;
7. High Energy Beam Transport channel (HEBT);
8. area where the therapeutical beam is used to irradiate patients with fixed and, if desired, rotating beams (excentric and/or isocentric gantries);
9. accelerating module of the DTL structure;
10. an accelerating module of the CCL structure;
11. input ports of the radiofrequency power;
12. distributed computer system;
12A and 12B first and second group of 12;
F direction of the beam for proton therapy.

Referring now to FIG. 1, according to the invention the proton accelerator complex substantially includes two kinds of accelerators 3 and 6 serially connected, namely a cyclotron 3 and a modular linac 6, for example of the type disclosed in WO 2004/054331 or in U.S. Pat. No. 6,888,326 B2 by the Applicant which are here quoted as a reference. The cyclotron 3 can be either at room temperature or superconducting.

It has to be remarked that the cyclotron 3 output energy is usually fixed and therefore its value will be chosen according to the desired application, and, more precisely, according to the type of centre that one wants to develop and/or the kind of isotope production and therapy.

The cyclotron is fed by either an internal or external source via, usually, a low energy beam transport line 2 (LEBT). According to the invention, the cyclotron extraction system allows simultaneous or alternate production of one or more beams, two of them are indicated in FIG. 1 as 4A and 4B, some of them are dedicated to radioisotope production for diagnostic and/or therapeutic purposes and possibly also to the production of tracers for industrial applications. The ratio of the currents in the two extracted beams can be adjusted for instance by varying the widths of the extracting foils if such extraction method is used.

The techniques employed for medical applications are, for example, those disclosed in U.S. Pat. No. 4,882,142 for the use of Sm-153, Gd-159 and Ho-166 chelated with DOTMP for suppression of bone marrow activity, or in U.S. Pat. No. 6,274,118 for identification and location of neuro-endocrine tumours directly or indirectly using agents chelating F-18, P-32, Ga-67, Br-77, Y-90, Tc-99m, In-111, I-123, I-125, Sm-153, I-131, Re-188, Tl-201, and or in EP No. 291,605-A and in U.S. Pat. No. 4,898,724 for the employment of Sm-153, Gd-159 and Ho-166 chelated with EDTMP for the bone medullar suppression and in the leukaemia therapy.

Other beams from the cyclotron can be used for neutron production which, properly slowed down, are used for the production of special radioisotopes, as disclosed for example in publication US 2005/00822469 A1, or for BNCT, as disclosed in patents U.S. Pat. Nos. 5,903,622 and 5,920,601, or for BNCS, as disclosed in U.S. Pat. No. 5,976,066.

In practice, one or more beams from the cyclotron 3 are conveyed to a matching section or to a Medium Energy Beam Line 5 (MEBT), in which magnetic lenses and well known mechanical or electromechanical chopper devices allow the interruption and/or the variation of the current injected in the radiofrequency linac 6. The beam injected into the linac is usually time modulated at the linac repetition rate (typically 100-400 Hz) and its intensity adjusted accordingly to the therapy requirements. Said time modulation, useful to avoid strong irradiation of the components of the MEBT 5 and the linac 6, and said intensity modulation are obtained acting on the source or on the LEBT 2 or on the MEBT 5 or on a combination of said elements as well. Moreover, in order to use the spot scanning technique mentioned above it is worthwhile finely adjusting the current intensity injected into the linac 6 in the time interval between the linac 6 pulses, while there is no linac 6 output beam and the location of dose deposition is moved to the next spot.

As well known, the technology of radiofrequency linacs is currently used for the acceleration of charged particles starting from an "ion source" up to the desired energy. According to the invention, the source of the radiofrequency linac 6 is the proton cyclotron 3, which is at the same time also used for radioisotope and/or neutron production.

The proton velocity range covered by linac 6 goes from the cyclotron 3 output velocity to the velocity determined by the maximum energy required for the requested therapy. To define these velocities one the parameter $\beta$ is normally used which is defined as the ratio between the velocity of the particle and the velocity of light. The required energy ranges are from a minimum of about 10 MeV to a maximum of about 70 MeV for the input energy of linac 6 (corresponding to the output energy of the cyclotron 3), whereas the output energy from the linac 6 required for protontherapy is between 60 MeV and 250 MeV, globally corresponding to $0.15 \leq \beta \leq 0.60$. The indicated $\beta$ values fall typically in the range of standing wave linacs. In these structures the accelerator is a resonant cavity inside of which intense oscillating electric fields result from the excitation of the cavity resonating modes.

In order to optimise the average accelerating field while minimizing power consumption, different structures can be used, each maximally efficient in a particularly range of $\beta$ values. Accordingly to the invention, in case of a low energy cyclotron injector 3 (i.e. 10-15 MeV) and when the maximum energy for therapy is requested, it is convenient to split linac 6 in two linacs 6A and 6B with different characteristics. More precisely one can use a drift tube linac 6A (DTL) and a coupled cavity linac 6B (CCL) which are mounted in cascade. In the invention it is foreseen to minimise the installed power of the linac 6 system by changing the structure at the energy at which the DTL 6A consumes more that the CCL 6B, this typically occurring at about $\beta \approx 0.4$ (100 MeV). However it is possible to extend the use of the CCL 6B to lower energies or the DTL 6A to higher energies, so to employ just one linac typology and avoid system complexity and related higher construction costs.

The linacs 6A and 6B have different possible realisations, but are always composed of several modules 9 and 10 with several power input ports 11. Each module of the DTL 6A and of the CCL 6B sections contains a number of accelerating cells and some focusing components. The focusing components are typically quadrupole magnets, either permanent or powered by a continous current.

According to the invention, for what concerns the DTL 6A one can use either a structure working in the transverse magnetic field mode (TM, called also E-mode) or a structure working in the transverse electric field mode (TE, called also H-mode) intrinsically more efficient at low energies with respect to the TM mode. Inversely, at higher energies the possible CCL 6B commonly employs the TM mode, more efficient at these energies.

According to the present invention for the DTL 6A one can foresee the employment of a TE mode structure of the CLUSTER type (as disclosed in the mentioned WO 2004/054331 and U.S. Pat. No. 6,888,236 B2) or of a TM mode structure of the type Side-Coupled Drift Tube Linac (SCDTL). In SCDTL structures well known short DTL structures working in TM mode are coupled together, as mentioned in FR-A-2 737 834.

Moreover, according to the invention, for the CCL linac 6B it is foreseen a Side-Coupled type linac working at high frequency, having similar characteristics of an accelerator already experimented by the inventor in the field of protontherapy [see U. Amaldi et al., "A Linac-booster for Protontherapy: Construction and Tests of a Prototype", Nucl. Instr Meth. Phys. Res. A521 (2004) 512-529].

It is important to note that the efficiency and the compactness of the complex is related to a high working frequency ($\geq 1$ GHz), which is new for proton linacs. In fact, according to the Kilpatrick law, higher frequencies allow larger accelerating field because, as is well known, if the geometry of the structure is scaled with the frequency, the effective "shunt impedance" per unit length—which is proportional to the accelerator efficiency—increases almost proportionally to the square root of the frequency. This implies an increase of the energy gain per unit length and, as a result, a proportional decrease of the total length of the accelerator. This is a crucial parameter in medical applications, where the reduction of the accelerator length is linked to the request of minimisation of the installation area.

A high frequency implies accelerating cells with a small beam-hole diameter. This is not a problem because of the low currents required for protontherapy (order of 1 nA) and the high current output of the cyclotrons used for radioisotope production (order of 100 µA).

Because the cyclotron current is bunched at typical frequencies of the order of 50 MHz, many tens of these bunches are contained in a proton pulse lasting 1-5 microseconds. The protons in a pulse are accelerated by the linac 6 every 2-10 milliseconds so that the duty cycle (i.e. the ratio between the duration of the proton pulse and the time separation between two successive pulses) is about $10^{-3}$. Since the linac accepts 'longitudinally' only about 10% of eachv cyclotron bunch, the cyclotron average current is reduced 'longitudinally' by an overall factor of the order of $10^{-4}$. 'Transversally', the linac 6 acceptance is often smaller than the cyclotron 3 emittance and the loss factor can be as small as $2 \cdot 10^{-3}$.

Therefore, the global loss factor between the output of cyclotron 3 and the output of the linac 6 is about $2 \cdot 10^{-5}$, a small number indeed but sufficient since the current needed for proton therapy is of the order of 0.1-5 nanoampere. (The lower limit corresponds to the requirements of "active" dose delivery systems, as with the spot scanning technique mentioned before; the upper limit is required when "passive" dose delivery methods are used). Even with the loss factor is as small as $2 \cdot 10^{-5}$, it suffices a cyclotron output current of 5-250 microampere, which can be produced by the cyclotrons commonly employed in the production of radioisotopes for medical and/or industrial purposes.

In substance the invention exploits the large ratio existing between the proton high current required for the radioisotope production and the low current needed for proton therapy. Given these circumstances, the installation of a high gradient, low duty cycle linac 6 downstream a high current cyclotron 3 is logic and efficient.

Finally, an important and novel feature of the invention is the said possibility of adjusting in about one millisecond the energy of the ouput protons of linacs 6A and 6B by varying the power levels and the phases of the signals that drive the klystrons powering the accelerating. The resulting pulsed time structure of the therapeutic beam is better fit to active systems of dose delivery, particularly to the said spot scanning technique developed at PSI (Villigen-Switzerland), than the one produced by cyclotrons and synchrotrons.

The operation of the cyclotron and of the linac modules, as well as the distribution of the different beams for proton-therapy and radioisotope production, are under the control of a distributed system of computers, schematically shown as 12. The supervision and control system includes, as an example, a first group of computers 12A—composed of about ten computers and used by the operators for the different procedures, a second group 12B—composed of about thirty computers for the control of the high technology apparata, and the software which allows the production and distribution, in parallel or alternated modes, of the proton beams. The said system is based on commercial components and languages provided by leading companies. In this way the long term reliability and maintenance of the system can be guaranteed. These companies are represented, as example, by National Instruments Italy S.r.l., Via Anna Kuliscioff 22 Milano, Italy for the front-end electronics, the managing software, and the real-time operating systems. Oracle Italia s.r.l., V.le Ercole Marelli 303 Sesto S. Giovanni, Italy could be, for instance, the supplier for the database and management of the data which transit in the supervision and control system. The operating systems and all applications which are not real-time could be based, as en example, on products supplied by Microsoft Italia, Via Rivoltana 13 Segrate, Italy.

To obtain the required speed (the timing system produces pulses with a resolution of few nanoseconds) and reliability in the management of the proton beams a modern approach in the development and management of the software has to be used. This approach is based on a tight integration among electronics, firmware and software in an architecture that replaces the development of ad hoc electronics with electronics "configurable" with suitable firmware codes. A further innovation consists in the introduction of "intelligent" behaviours through dedicated processors equipped with appropriate firmware which replace the old electronics logic. The proposed task distribution guarantees good overall performance because each device is self-dependent and it allows also continuous crosschecks to assure the correct operation of the whole system.

Three different schemes of the invention are presented as examples. The basic parameters of the first scheme are shown in Table 5. It is based on a cyclotron which accelerates the protons up to the energy of 30 MeV. The proton beam is then conveyed through the transport line MEBT 5 into a linac 6 which, in this case, is of a single type: SCL=Side-Coupled Linac. The example proposes a working frequency of 2998 GHz. The accelerating modules are feed by commercial radio-frequency amplifiers (klystrons) produced, for example, by the company Thales electron devices, (Latecoere, 78941 Velizy Cedex, France).

TABLE 5

Example of a linac which accelerates protons from 30 MeV to 210 MeV

| | Type of linac SCL |
|---|---|
| Frequency [MHz] | 2998 |
| Input energy [MeV] | 30 |
| Output energy [MeV] | 210 |
| Number of accelerating cells per accelerating structure | 14 |
| Diameter of an accelerating cell [mm] | 70 |
| Diameter of the beam hole [mm] | 8 |
| Maximum mechanical tolerance of the cells [mm] | ±0.01 |
| Number of accelerating structures per module | 2 |
| Number of modules (equivalent to number of klystrons) | 20 |
| Module length (injection-extraction) [m] | 0.53-1.08 |
| Total length of the linac [m] | 16.4 |
| Average transit time factor | 0.85 |
| Effective shunt impedance $ZT^2$ [MΩ/m] | 22-69 |
| Average axial electric field [MV/m] | 16.7-19.0 |
| Maximum uniformity of the electric field in the accelerating cells [%] | ±3 |
| Kilpatrick number defining the maximum electric field on the surface | 1.8 |
| Repetition rate of the proton pulses [Hz] | 200 |
| Pulse length[μs] | 2-5 |
| RF power uniformity in a pulse [%] | ±0.5 |
| RF power stability [%] | ±0.2 |
| Peak power per module [MW] | 3 |
| Average power per module (pulses: 2 μs-5 μs) [kW] | 1.5-3.0 |
| Power required by the linac [kW] | 30-61 |
| Duty cycle [%] | 0.04-0.1 |
| Synchronous phase | −15° |
| Length of the magnetic quadrupole [mm] | 30 |
| Diameter of the magnetic quadrupole aperture [mm] | 10 |
| Maximum misalignment for the magnetic quadrupoles [mm] | ±0.1 |
| Magnetic gradient of the quadrupole [T/m] (FODO configuration) | 170-130 |
| Normalized transversal acceptance [π mm mrad] | 3.4 |
| Length of the stable region (bucket) in the longitudinal phase-space (injection-extraction) | 45°-20° |
| Height of the stable region (bucket) in the longitudinal phase-plane (injection-extraction) [MeV] | ±0.3-±0.7 |
| Phase advance of the synchrotronic oscillation per accelerating unit (injection-extraction) | 45°-24° |
| Phase advance of the betatronic oscillation per focalization period (injection-extraction) | 74°-45° |
| Working temperature [° C.] | 26 |
| Thermal stability of the cooling water [° C.] | ±0.4 |
| Flux of the cooling water [l/min] | 60 |
| Nominal vacuum [mbar] | 10-6 |

In the second example the cyclotron accelerates the protons to 15 MeV and the linac is composed of a CLUSTER section from 15 MeV to 67 MeV and a SCL section from 67 MeV to 210 MeV. To improve the linac efficiency and to reduce the overall length, CLUSTER works at 1.5 GHz and the SCL at 3 GHz.

TABLE 6

Example of a linac which accelerates protons from 15 MeV to 210 Me

| | Type of linac | |
|---|---|---|
| | DTL | SCL |
| Frequency [MHz] | 1499 | 2998 |
| Input energy [MeV] | 15 | 67 |
| Output energy [MeV] | 67 | 210 |
| Number of accelerating cells per accelerating structure | 7 | 14 |
| Diameter of an accelerating cell [mm] | 80 | 70 |
| Diameter of the beam hole [mm] | 8 | 8 |
| Maximum mechanical tolerance of the cells [mm] | ±0.02 | ±0.01 |
| Number of accelerating structures per module | 8-6-4—4 | 2 |
| Number of modules (in the case of the SCL linac it is equal to the number of klystrons) | 4 | 14 |
| Module length (injection-extraction) [m] | 2.01-1.37 | 0.69-1.08 |
| Total length of the linac [m] | 6.2 | 12.6 |
| Average transit time factor | 0.84 | 0.85 |
| Effective shunt impedance $ZT^2$ [MΩ/m] | 66-61 | 43-69 |
| Average axial electric field [MV/m] | 15-15.3 | 18.6-19.0 |
| Maximum uniformity of the electric field in the accelerating cells [%] | ±3 | ±3 |
| Kilpatrick number defining the maximum electric field on the copper surface | 2.1 | 1.8 |
| Repetition rate of the proton pulses [Hz] | 200 | 200 |
| Pulse length[μs] | 2-5 | 2-5 |
| RF power uniformity in a pulse [%] | ±0.5 | ±0.5 |
| RF power stability [%] | ±0.2 | ±0.2 |
| Peak power per module [MW] | 2.5-3.3 | 3—3 |
| Average power per module (pulses: 2 μs-5 μs) [kW] | 1.5-3 | 1.5-3 |
| Power required by the linac [kW] | 6-12 | 21-42 |
| Duty cycle [%] | 0.04-0.1 | 0.04-0.1 |
| Synchronous phase | −13° | −15° |
| Length of the magnetic quadrupole [mm] | 30 | 30 |
| Diameter of the magnetic quadrupole aperture [mm] | 10 | 10 |
| Maximum misalignment for the magnetic quadrupoles [mm] | ±0.1 | ±0.1 |
| Magnetic gradient of the quadrupole [T/m] (FODO configuration) | 156-144 | 170-130 |
| Normalized transversal acceptance [π mm mrad] | 3.3 | 4.0 |
| Length of the stable region (bucket) in the longitudinal phase-space (injection-extraction) | 39°-22° | 45°-29° |
| Height of the stable region (bucket) in the longitudinal phase-plane (injection-extraction) [MeV] | ±0.2-±0.3 | ±0.6-±0.9 |
| Phase advance of the synchrotronic oscillation per accelerating unit (injection-extraction) | 37°-23° | 45°-24° |
| Phase advance of the betatronic oscillation per focalization period (injection-extraction) | 93°-69° | 74°-45° |
| Working temperature [° C.] | 26 | 26 |
| Thermal stability of the cooling water [° C.] | ±0.6 | ±0.4 |
| Flux of the cooling water [l/min] | 65 | 60 |
| Nominal vacuum [mbar] | $10^{-6}$ | $10^{-6}$ |

In the third example the cyclotron accelerates the protons up to 72 MeV and the linac, which is of the SCL type, accelerates the protons from 72 MeV to 240 MeV.

TABLE 7

Example of a linac which accelerates protons from 72 MeV to 240 MeV

| | Type of linac SCL |
|---|---|
| Frequency [MHz] | 2998 |
| Input energy [MeV] | 72 |
| Output energy [MeV] | 240 |
| Number of accelerating cells per accelerating structure | 16 |
| Diameter of an accelerating cell [mm] | 70 |
| Diameter of the beam hole [mm] | 8 |
| Maximum mechanical tolerance of the cells [mm] | ±0.01 |
| Number of accelerating structures per module | 2 |
| Number of modules (equivalent to number of klystrons) | 14 |
| Module length (injection-extraction) [m] | 0.80-1.26 |
| Total length of the linac [m] | 14.6 |
| Average transit time factor | 0.85 |
| Effective shunt impedance $ZT^2$ [MΩ/m] | 45-71 |
| Average axial electric field [MV/m] | 18.2-18.5 |
| Maximum uniformity of the electric field in the accelerating cells [%] | ±3 |
| Kilpatrick number defining the maximum electric field on the copper surface | 1.8 |
| Repetition rate of the proton pulses [Hz] | 200 |
| Pulse length[μs] | 2-5 |
| RF power uniformity in a pulse [%] | ±0.5 |
| RF power stability [%] | ±0.2 |
| Peak power per module [MW] | 3.3 |
| Average power per module (pulses: 2 μs-5 μs) [kW] | 1.7-3.3 |
| Power required by the linac [kW] | 23-46 |
| Duty cycle [%] | 0.04-0.1 |
| Synchronous phase | −15 |
| Length of the magnetic quadrupole [mm] | 30 |
| Diameter of the magnetic quadrupole aperture [mm] | 10 |
| Maximum misalignment for the magnetic quadrupoles [mm] | ±0.1 |
| Magnetic gradient of the quadrupole [T/m] (FODO configuration) | 166-128 |
| Normalized transversal acceptance [π mm mrad] | 3.9 |
| Length of the stable region (bucket) in the longitudinal phase-space (injection-extraction) | 45°-28° |
| Height of the stable region (bucket) in the longitudinal phase-plane (injection-extraction) [MeV] | ±0.7-±0.8 |
| Phase advance of the synchrotronic oscillation per accelerating unit (injection-extraction) | 39°-25° |
| Phase advance of the betatronic oscillation per focalization period (injection-extraction) | 74°-48° |
| Working temperature [° C.] | 26 |
| Thermal stability of the cooling water [° C.] | ±0.4 |
| Flux of the cooling water [l/min] | 65 |
| Nominal vacuum [mbar] | $10^{-6}$ |

The three schemes make use of commercial permanent magnetic quadrupoles for the transversal focalization. These quadrupoles are very small in order to be introduced inside the linac; they are housed in between the accelerating structures to form a FODO lattice.

The above description of the structure and functions of three examples of the accelerating complex called PACRIT shows that said complexes achieves the mentioned objectives and obtains the mentioned advantages. From the above description it is clear that the examples and the proposed components have only an exemplificative purpose. Those skilled in the art could introduce modifications, for example with the employment/substitution of single components and/or a software system or single software components with a novel/equivalent software system and/or software components. All the possible modifications remain, in any case, within the scope and the spirit of the present invention as claimed in the following claims.

LITERATURE

The following is a list of publications in the field of hadrontherapy and in the field of accelerators for hadrontherapy. The inventor is author or co-author of several of the listed publications.

U. Amaldi and B. Larsson (Eds.), "Hadrontherapy in Oncology", Elsevier Science B. V., Amsterdam, the Netherlands, 1994. ISBN 0-444-81918-5.

U. Amaldi and M. Silari (Eds.), "The TERA Project and The Centre for Oncological Hadrontherapy, Vol. I, Vol. II", INFN-LNF Frascati, Italy, 1995. ISBN 88-86409-09-5. The "Blue Book".

U. Amaldi, M. Grandolfo and L. Picardi (Eds.), "The RITA Network and the Design of Compact Proton Accelerators", INFN-LNF Frascati, Italy, 1996. ISBN 88-86409-08-7. The "Green Book".

U. Amaldi, "Cancer Therapy with Particle Accelerators", Nucl. Phys. A654 (1999) 375-399.

A. Brahme, R. Lewensohn, U. Ringborg, U. Amaldi, F. Gerardi and S. Rossi, "Design of a centre for biologically optimised light ion therapy in Stockholm", Nucl. Instr Meth. Phys. Res. B184 (2001) 569-588.

M. Goitein, A. Lomax and E. Pedroni, "Treating Cancer with Protons", Phys. Today 55 (2002) 45-50.

M. Goitein and M. Jermann, "The Relatice Costs of Proton and X-ray Radiation Therapy", Clin. Oncol. 15 (2003) 537-550.

U. Amaldi et al., "A Linac-booster for Protontherapy: Construction and Tests of a Prototype", Nucl. Instr Meth. Phys. Res. A521 (2004) 512-529.

U. Amaldi, M. Crescenti, R. Zennaro, "Linac for Ion Beam Acceleration", U.S. Pat. No. 6,888,326; WO 2004/054331 A1.

U. Amaldi, M. Crescenti, R. Zennaro, "Ion Acceleration System for Hadrontherapy" PCT/EP2005/011568

U. Amaldi and G. Kraft, "Radiotherapy with Beams of Carbon Ions", Rep. Prog. Phys 68 (2005) 1861-1882.

The invention claimed is:

1. An accelerator complex of proton beams, comprising:
a cyclotron with a plurality of beam lines, each beam line configured to provide a proton beam generated by the cyclotron;
a proton source configured to provide protons to the cyclotron;
a target, configured with a first of the beam lines to produce radioisotopes;
a proton radiofrequency linear accelerator (LINAC), comprised of LINAC accelerating modules and configured to accelerate one of the proton beams generated by the cyclotron;
a Medium Energy Beam Transfer channel (MEBT), connected to a second of the beam lines output from the cyclotron on a first side of the MEBT to receive a proton beam of the second beam line, and to a beam input of the radiofrequency LINAC on a second side of the MEBT to provide the proton beam to the radiofrequency LINAC, the MEBT equipped with one or more mechanical and/or magnetic and/or electrostatic "choppers" and "gates" configured i) to improve security, ii) to reduce irradiation of components located downstream of the MEBT, and iii) to vary an intensity of the beams accelerated by the LINAC for proton therapy;
a High Energy Beam Transfer channel (HEBT), connected to an output of the radiofrequency LINAC on a first side of the HEBT to receive a high energy proton beam from the LINAC, and to one or more systems for distribution of a proton dose to a patient on a second side of the HEBT;
a modular power system for supplying radiofrequency power to the LINAC accelerating modules, the power system configured to power, in a separate and independent way, one or more of said accelerating modules; and
a fully integrated computer control system configured to control the accelerator complex,
wherein the accelerator complex is configured to perform, alternatively or simultaneously, any of radioisotope production for medical or industrial purposes, and irradiation of shallow and/or deep-seated tumors, and
wherein the integrated computer control system is composed of a distributed system of computers formed by a first group of computers dedicated to operators and to foreseen procedures, and a second group of computers dedicated to high technology apparata, and a specific software configured to operate the different proton beams both in parallel and one at a time.

2. The accelerator complex for protons according to claim 1, wherein said proton source is one of Multicusp, ECR, and EBIS.

3. The accelerator complex for protons according to claim 1, wherein said proton source as connected to the cyclotron through a Low Energy Beam Transport channel (LEBT) configured to pulse and/or vary an intensity of proton pulses accelerated in the cyclotron and in the LINAC.

4. The accelerator complex for protons according to claim 1, wherein the proton beam entering the radiofrequency LINAC is one of continuous and pulsed according to a repetition rate of said radiofrequency LINAC.

5. A method of proton beams acceleration for alternate or simultaneous use in diagnostics and protontherapy by using an accelerator complex for protons according to claim 1, comprising the step of:
producing neutrons for the production of radioisotopes and/or for BNCT and/or for BNCS.

6. The accelerator complex for protons according to claim 1, wherein said radiofrequency LINAC has a resonant frequency larger or equal to 1 GHz.

7. The accelerator complex for protons according to claim 1, wherein said radiofrequency LINAC has a modular structure, including a first accelerating section of a DTL type and a successive second accelerating section of a CCL type, and
wherein the radiofrequency power is distributed in an adjustable and independent manner to one of i) each of the accelerating modules and ii) a group of the accelerating modules.

8. The accelerator complex for protons according to claim 1,
wherein the radiofrequency LINAC has a modular structure is composed of a variable number of accelerating modules, and
said accelerating modules of the modular structure are not all aligned on a same geometrical straight line.

9. The accelerator complex for protons according to claim 1, wherein the radiofrequency power system, is separated to facilitate substitution of the power system and repair of the power system in case of failure.

10. The accelerator complex for protons according to claim 1, wherein said radiofrequency power system is composed of power supply modules configured to control an amplitude and a phase of a radiofrequency signal sent to the accelerating modules, said power supply modules configured to adjust an energy of the beam sent to proton therapy rooms.

11. The accelerator complex for protons according to claim 1, wherein said cyclotron pre-accelerates the proton beams generated by the cyclotron up to a maximum energy in a range from about 10 to about 100 MeV.

12. The accelerator complex for protons according to claim 7, wherein said first and second accelerating sections of the radiofrequency LINAC operate at the same frequency.

13. The accelerator complex for protons according to claim 1, wherein the radiofrequency LINAC is configured with a CCL structure, and configured to accelerate protons from 30 MeV, the LINAC configured to operate with a frequency of 2.998 GHz and with substantially the following parameters:

|  | Type of LINAC SCL |
|---|---|
| Frequency [MHz] | 2998 |
| Input energy [MeV] | 30 |
| Output energy [MeV] | 210 |
| Number of accelerating cells per accelerating structure | 14 |
| Number of accelerating structures per module | 2 |
| Number of modules (equivalent to number of klystrons) | 20 |
| Total length of the LINAC [m] | 16.4 |
| Repetition rate of the pulses [Hz] | 200 |
| Pulse length[µs] | 2-5 |
| Average power per module (pulses: 2 µs-5 µs) [kW] | 1.5-3.0 |
| Power required by the LINAC [kW] | 30-61 |
| Duty cycle [%] | 0.04-0.1 |
| Magnetic gradient of the quadrupoles [T/m] | 170-130 |
| Normalized transversal acceptance [π mm mrad] | 3.4 |

14. The accelerator complex for protons according to claim 7, wherein the first and second accelerating sections are configured to accelerate protons from 15 MeV, wherein the first accelerating section of the DTL type is configured at a frequency of 1.499 GHz, wherein the second accelerating section of the CCL type is configured at a frequency 2.998 GHz, and wherein the LINAC is configured to operate with substantially the following parameters:

|  | Type of LINAC | |
|---|---|---|
|  | DTL | SCL |
| Frequency [MHz] | 1499 | 2998 |
| Input energy [MeV] | 15 | 67 |
| Output energy [MeV] | 67 | 210 |
| Number of accelerating cells per accelerating structure | 7 | 14 |
| Number of accelerating structures per module | 8-6-4—4 | 2 |
| Number of modules (equivalent to number of klystrons) | 4 | 14 |
| Total length of the LINAC [m] | 6.2 | 12.6 |
| Repetition rate of the pulses [Hz] | 200 | 200 |
| Pulse length[µs] | 2-5 | 2-5 |
| Average power per module (pulses: 2 µs-5 µs) [kW] | 1.5-3 | 1.5-3 |
| Power required by the LINAC [kW] | 6-12 | 21-42 |
| Duty cycle [%] | 0.04-0.1 | 0.04-0.1 |
| Magnetic gradient of the quadrupole [T/m] (FODO configuration) | 156-144 | 170-130 |
| Normalized transversal acceptance [π mm mrad] | 3.3 | 4.0 |

15. The accelerator complex for protons according to claim 1, wherein the radiofrequency LINAC is configured with a CCL structure, and configured to accelerate protons from 72 MeV, the LINAC configured to operate with a frequency of 2.998 GHz and with substantially the following parameters:

|  | Type of LINAC SCL |
|---|---|
| Frequency [MHz] | 2998 |
| Input energy [MeV] | 72 |
| Output energy [MeV] | 240 |
| Number of accelerating cells per accelerating structure | 16 |
| Number of accelerating structures per module | 2 |
| Number of modules (equivalent to number of klystrons) | 14 |
| Total length of the LINAC [m] | 14.6 |
| Repetition rate of the pulses [Hz] | 200 |
| Pulse length[µs] | 2-5 |
| Average power per module (pulses: 2 µs-5 µs) [kW] | 1.7-3.3 |
| Power required by the LINAC [kW] | 23-46 |
| Duty cycle [%] | 0.04-0.1 |
| Magnetic gradient of the quadrupole [T/m] (FODO configuration) | 166-128 |
| Normalized transversal acceptance [π mm mrad] | 3.9 |

16. A method of proton beams acceleration for alternate, or simultaneous use in diagnostics and protontherapy by using an accelerator complex for protons according to claim 1, comprising the steps of:

producing the protons with the proton source;

injecting the protons in the cyclotron;

continuously extracting proton beams from the cyclotron in two or more beam lines;

feeding at least one beam line with a proton beam for protontherapy;

injecting the proton beam in the radiofrequency LINAC;

accelerating the proton beam in the radiofrequency LINAC to obtain, at an output of the LINAC, a protontherapy beam of a desired variable output energy and intensity and with a pulsed time structure, the protontherapy beam configured to perform active spot scanning and passive scanning on the patient;

distributing the protontherapy beam one or more rooms; and feeding at least two other beam lines, in alternation or simultaneously, with another proton beam for isotope production.

17. The method of proton beams acceleration according to claim 16, further comprising the step of:

prior to injecting the proton beam in the radiofrequency LINAC, gating and chopping the proton beam in the at least one beam line.

18. A method of proton beams acceleration for alternate or simultaneous use in diagnostics and protontherapy, comprising the step of:

using an accelerator complex of proton beams, wherein the accelerator complex comprises, a cyclotron with a plurality of beam lines, each beam line configured to provide a proton beam generated by the cyclotron, a proton source configured to provide protons to the cyclotron, a target, configured with a first of the beam lines to produce radioisotopes, a proton radiofrequency linear accelerator (LINAC), comprised of LINAC accelerating modules and configured to accelerate one of the proton beams generated by the cyclotron, a Medium Energy Beam Transfer channel (MEBT), connected to a second of the beam lines output from the cyclotron on a first side of the MEBT to receive a proton beam of the second beam line, and to a beam input of the radiofrequency LINAC on a second side of the MEBT to provide the proton beam to the radiofrequency LINAC, the MEBT equipped with one or more mechanical and/or magnetic and/or electrostatic "choppers" and "gates" configured i) to improve security, ii) to reduce irradiation of components located downstream of the MEBT, and iii) to vary an intensity of the beams accelerated by the LINAC for proton therapy, a High Energy Beam Transfer channel (HEBT), connected to an output of the radiofrequency LINAC on a first side of the HEBT to receive a high energy proton beam from the LINAC, and to one or more systems for distribution of a proton dose to a patient on a second side of the HEBT;

a modular power system for supplying radiofrequency power to the LINAC accelerating modules, the power system configured to power, in a separate and independent way, one or more of said accelerating modules, and a fully integrated computer control system configured to control the accelerator complex, wherein the accelerator complex is configured to perform, alternatively or simultaneously, any of radioisotope production for medical or industrial purposes, and irradiation of shallow and/or deep-seated tumors, and wherein the using step comprises the sub-steps of:

producing the protons with the proton source;

injecting the protons in the cyclotron;

continuously extracting proton beams from the cyclotron in two or more beam lines;

feeding at least one beam line with a proton beam for protontherapy;

injecting the proton beam in the radiofrequency LINAC;

accelerating the proton beam in the radiofrequency LINAC to obtain, at an output of the LINAC, a protontherapy beam of a desired variable output energy and intensity and with a pulsed time structure, the protontherapy beam configured to perform active spot scanning and passive scanning on the patient;

distributing the protontherapy beam one or more rooms; and feeding at least two other beam lines, in alternation or simultaneously, with another proton beam for isotope production.

19. The method of proton beams acceleration according to claim 18, further comprising the step of:

prior to injecting the proton beam in the radiofrequency LINAC, gating and chopping the proton beams in the at least one beam line.

20. An accelerator complex of proton beams, comprising:

a cyclotron with a plurality of beam lines, each beam line configured to provide a proton beam generated by the cyclotron;

a proton source configured to provide protons to the cyclotron;

a target, configured with a first of the beam lines to produce radioisotopes;

a proton radiofrequency linear accelerator (LINAC), comprised of LINAC accelerating modules and configured to accelerate one of the proton beams generated by the cyclotron;

a Medium Energy Beam Transfer channel (MEBT), connected to a second of the beam lines output from the cyclotron on a first side of the MEBT to receive a proton beam of the second beam line, and to a beam input of the radiofrequency LINAC on a second side of the MEBT to provide the proton beam to the radiofrequency LINAC, the MEBT equipped with one or more mechanical and/or magnetic and/or electrostatic "choppers" and "gates" configured i) to improve security, ii) to reduce irradiation of components located downstream of the MEBT, and iii) to vary an intensity of the beams accelerated by the LINAC for proton therapy;

a High Energy Beam Transfer channel (HEBT), connected to an output of the radiofrequency LINAC on a first aide of the HEBT to receive a high energy proton beam from the LINAC, and to one or more systems for distribution of a proton dose to a patient on a second side of the HEBT;

a modular power system for supplying radiofrequency power to the LINAC accelerating modules, the power system configured to power, in a separate and independent way, one or more of said accelerating module; and a fully integrated computer control system configured to control the accelerator complex, wherein the accelerator complex is configured to perform, alternatively or simultaneously, any of radioisotope production for medical or industrial purposes, and irradiation of shallow and/or deep-seated tumors, wherein said radiofrequency LINAC has a modular structure, including a first accelerating section of a DTL type and a successive second accelerating section of a CCL type, wherein the radiofrequency power is distributed in an adjustable and independent manner to one of i) each of the accelerating modules and ii) a group of the accelerating modules, wherein the first and second accelerating sections are configured to accelerate protons from 15 MeV, wherein the first accelerating section of the DTL type is configured at a frequency of 1.499 GHz, wherein the second accelerating section of the CCL type is configured at a frequency 2.999 GHz, and wherein the LINAC is configured to operate with substantially the following parameters:

| Type of LINAC | DTL | SCL |
| --- | --- | --- |
| Frequency [MHz] | 1499 | 2998 |
| Input energy [MeV] | 15 | 67 |
| Output energy [MeV] | 67 | 210 |

-continued

| Type of LINAC | DTL | SCL |
|---|---|---|
| Number of accelerating cells per accelerating structure | 7 | 14 |
| Number of accelerating structures per module | 8 - 6 - 4 - 4 | 2 |
| Number of modules (equivalent to number of klystrons) | 4 | 14 |
| Total length of the LINAC [m] | 6.2 | 12.6 |
| Repetition rate of the pulses [Hz] | 200 | 200 |
| Pulse length [μs] | 2-5 | 2-5 |
| Average power per module (pulses: 2 μs-5 μs) [kW] | 1.5-3 | 1.5-3 |
| Power required by the LINAC [kW] | 6-12 | 21-42 |
| Duty cycle [%] | 0.04-0.1 | 0.04-0.1 |
| Magnetic gradient of the quadrupole [T/m] (FODO configuration) | 156-144 | 170-130 |
| Normalized transversal acceptance [π mm mrad] | 3.3 | 4.0 |

21. An accelerator complex of proton beams, comprising:
a cyclotron with a plurality of beam lines, each beam line configured to provide a proton beam generated by the cyclotron;
a proton source configured to provide protons to the cyclotron;
a target, configured with a first of the beam lines to produce radioisotopes;
a proton radiofrequency linear accelerator (LINAC), comprised of LINAC accelerating modules and configured to accelerate one of the proton beams generated by the cyclotron;
a Medium Energy Beam Transfer channel (MEBT), connected to a second of the beam lines output from the cyclotron on a first side of the MEBT to receive a proton beam of the second beam line, and to a beam input of the radiofrequency LINAC on a second side of the MEBT to provide the proton beam to the radiofrequency LINAC, the MEBT equipped with one or more mechanical and/or magnetic and/or electrostatic "choppers" and "gates" configured i) to improve security, ii) to reduce irradiation of components located downstream of the MEBT, and iii) to vary an intensity of the beams accelerated by the LINAC for proton therapy;
a High Energy Beam Transfer channel (HEBT), connected to an output of the radiofrequency LINAC on a first side of the HEBT to receive a high energy proton beam from the LINAC, and to one or more systems for distribution of a proton dose to a patient on a second aide of the HEBT;
a modular power system for supplying radiofrequency power to the LINAC accelerating modules, the power system configured to power, in a separate and independent way, one or more of said accelerating modules; and
a fully integrated Computer control system configured to control the accelerator complex,
wherein the accelerator complex is configured to perform, alternatively or simultaneously, any of radioisotope production for medical or industrial purposes, and irradiation of shallow and/or deep-seated tumors, and
wherein the radiofrequency LINAC is configured with a CCL structure, and configured to accelerate protons from 72 MeV, the LINAC configured to operate with a frequency of 2.998 GHz and with substantially the following parameters:

| Type of LINAC | SCL |
|---|---|
| Frequency [MHz] | 2998 |
| Input energy [MeV] | 72 |
| Output energy [MeV] | 240 |
| Hunter of accelerating cells per accelerating structure | 16 |
| Number of accelerating structures per module | 2 |
| Number of modules (equivalent to number of klystrons) | 14 |
| Total length of the LINAC [m] | 14.6 |
| Repetition rate of the pulses [Hz] | 200 |
| Pulse length [μs] | 2-5 |
| Average power per module (pulses: 2 μs-5 μs ) [kW] | 1.7-3.3 |
| Power required by the LINAC [kW] | 23-46 |
| Duty cycle [%] | 0.04-0.1 |
| Magnetic gradient of the quadrupole [T/m] (FODO configuration) | 166-128 |
| Normalized transversal acceptance [π mm mrad] | 3.9 |

* * * * *